(12) United States Patent
Auriel et al.

(10) Patent No.: US 11,712,521 B2
(45) Date of Patent: Aug. 1, 2023

(54) INJECTION NOZZLE FOR A NEEDLELESS INJECTION DEVICE

(71) Applicant: CROSSJECT, Dijon (FR)

(72) Inventors: Christophe Auriel, Binges (FR); Patrick Alexandre, Gray (FR); Benoit Guichard, Dijon (FR); Jennifer Ascani, Sivry Ante (FR); M. Abdel Tazibt, Bettancourt la Ferree (FR)

(73) Assignee: CROSSJECT, Dijon (FR)

( * ) Notice: Subject to any disclaimer, the term of this patent is extended or adjusted under 35 U.S.C. 154(b) by 0 days.

(21) Appl. No.: 16/381,584

(22) Filed: Apr. 11, 2019

(65) Prior Publication Data

US 2019/0231981 A1 Aug. 1, 2019

Related U.S. Application Data

(63) Continuation of application No. PCT/FR2017/052701, filed on Oct. 2, 2017.

(30) Foreign Application Priority Data

Oct. 11, 2016 (FR) ..................................... 1659833

(51) Int. Cl.
*A61M 5/30* (2006.01)
*A61M 5/20* (2006.01)

(52) U.S. Cl.
CPC ........ *A61M 5/3007* (2013.01); *A61M 5/2046* (2013.01); *A61M 2205/8218* (2013.01)

(58) Field of Classification Search
CPC .... A61M 5/2046; A61M 5/3007; A61M 5/30; A61M 2205/8218; A61M 2005/8225; A61M 2205/8231; A61M 5/20; A61M 5/2053
See application file for complete search history.

(56) References Cited

U.S. PATENT DOCUMENTS

| 2,737,946 | A | * | 3/1956 | Hein, Jr. | ................. | A61M 5/30 604/70 |
| 3,515,130 | A | * | 6/1970 | Tsujino | ................... | A61M 5/30 604/70 |
| 6,056,716 | A | * | 5/2000 | D'Antonio | .............. | A61M 5/24 604/134 |

(Continued)

FOREIGN PATENT DOCUMENTS

| CN | 1361703 | 7/2002 |
| CN | 1399567 | 2/2003 |

(Continued)

OTHER PUBLICATIONS

International Search Report for International application PCT/FR2017/052701, dated Dec. 1, 2017.

*Primary Examiner* — Bradley J Osinski
(74) *Attorney, Agent, or Firm* — Burris Law, PLLC

(57) ABSTRACT

An injection nozzle for a needleless injection device includes at least one outlet conduit extending parallel to an injection axis (B). The outlet conduit(s) include a first conduit portion having a first section, a second conduit portion having a second section, the first section being larger than the second section, and a connecting portion between the first conduit portion and the second conduit portion. The connecting portion is inclined at an angle between 70° and 90° with respect to the injection axis (B).

14 Claims, 3 Drawing Sheets

(56) References Cited

U.S. PATENT DOCUMENTS

| | | | |
|---|---|---|---|
| 6,406,455 B1 | 6/2002 | Willis et al. | |
| 6,716,190 B1 * | 4/2004 | Glines | A61M 5/3007 604/141 |
| 7,744,563 B2 * | 6/2010 | Landau | A61M 5/2053 604/71 |
| 2007/0055200 A1 * | 3/2007 | Gilbert | A61M 5/30 604/70 |
| 2015/0374921 A1 * | 12/2015 | Kojic | B05B 1/02 239/1 |

FOREIGN PATENT DOCUMENTS

| | | |
|---|---|---|
| CN | 102458290 | 5/2012 |
| CN | 102648012 | 8/2012 |
| DE | 202010005982 | 7/2010 |
| JP | H05184674 | 7/1993 |
| JP | 2002539857 | 11/2002 |
| JP | 2006523484 | 10/2006 |
| WO | 1992008508 | 5/1992 |
| WO | 1995027523 | 10/1995 |
| WO | 2002034317 | 5/2002 |
| WO | 2008004337 | 1/2008 |
| WO | 2010108116 | 9/2010 |

\* cited by examiner

INJECTION NOZZLE FOR A NEEDLELESS INJECTION DEVICE

CROSS-REFERENCE TO RELATED APPLICATIONS

This application is a continuation of International Application No. PCT/FR2017/052701, filed on Oct. 2, 2017, which claims priority to and the benefit of FR 16/59833 filed on Oct. 11, 2016. The disclosures of the above applications are incorporated herein by reference.

FIELD

The present disclosure relates to needleless injection devices, prefilled and disposable, operating with a source of energy.

BACKGROUND

The statements in this section merely provide background information related to the present disclosure and may not constitute prior art.

The technical field relates to needleless injection devices, prefilled and disposable, operating with a source of energy such as for example a gas generator, and used for intradermal, subcutaneous and intramuscular injections of a liquid active ingredient for a therapeutic use in human and animal medicine.

The active ingredient is constituted by a liquid which is more or less viscous, a mixture of liquids, or a gel. The active ingredient may also be a solid dissolved in an appropriate solvent for injection or be constituted by a powdery solid suspended at a given concentration in an appropriate liquid. The grain-size distribution of the active ingredient should then be compatible with the diameter of the conduits in order to avoid plugging the latter.

In a manner known per se, such as for example in the patent application FR-A-2815544 (equivalent to WO 02/34317), an injection device includes a body successively comprising a gas generator, an expansion chamber, a reservoir containing the liquid active ingredient and an injection system.

The reservoir is constituted by a glass tube which is inserted into the body of the device and which is plugged by an upstream cap-plunger and a downstream cap-plunger between which the liquid active ingredient is contained.

The downstream free end of the reservoir cooperates with an injection nozzle which includes at least one injection conduit extending axially along an injection axis.

The gas generator is designed to generate a pressurized gas which drives in displacement the cap-plungers in order to inject the active ingredient through the skin of the patient throughout the injection nozzle.

In addition, the injection device includes a hollow cover which wraps the body and which delimits a lower opening adapted for the passage of the injection nozzle.

The free end of the injection nozzle which projects out of the body and of the cover is protected by a removable lid and a cap which houses the lid.

It is known to use bottle-like shaped nozzles, as represented in FIG. 4. By bottle-like shape, it is meant a shape comprising a first portion with a first section and a second portion with a second section, the first section being larger than the second section. The nozzle further comprises a connecting portion configured to connect the first and the second portion according to a slight inclination, for example at 45° with respect to the axis of the nozzle and whose angles are rounded.

The choice of this shape type directly arises from the state of the art relating to fluids mechanics. Indeed, this shape type is recommended to limit pressure drops and thus improve the performances of the liquid ingredient jet at the nozzle outlet.

Nonetheless, such a nozzle shape has a coherence length of the active ingredient jet which is not optimum with regards to the pressure exerted on the active ingredient.

SUMMARY

The present disclosure concerns an injection nozzle for a needleless injection device comprising an outlet conduit extending according to an injection axis, the at least one outlet conduit comprising:

a first conduit portion with a first section;

a second conduit portion with a second section, the first section being larger than the second section; and a connecting portion between the first conduit portion and the second conduit portion, the connecting portion being inclined by an angle comprised between 70° and 90° with respect to the injection axis.

Thanks to these arrangements, the coherence length of the fluid jet is improved. Indeed, the current lines are oriented so as to be substantially parallel to each other over a longer distance, enabling a better penetration and propagation of the product in human tissues.

Furthermore, unexpectedly in view of the general principles of fluids mechanics, the speed of the fluid at the outlet is higher by substantially 10% in comparison with a bottle-like shape, for the same pressure. Indeed, the bottle-like shape generally allows limiting pressure drops and therefore improving the fluid speed.

Furthermore, the arrangements according to the present disclosure allow limiting the consequences of a manufacturing defect. Furthermore, a connecting portion that is significantly inclined with respect to the injection axis is more easy to make and less expensive.

The arrangements according to the present disclosure allow either obtaining a better performance of the jet at the outlet of the injection nozzle with an identical pressure generated by the gas generator or preserving identical performances of the fluid jet at the outlet of the nozzle while reducing the pressure to be exerted by the gas generator, and thus saving energy.

According to other optional features according to the present disclosure:

the connecting portion is inclined by an angle comprised between 80° and 90°. These arrangements allow improving the performances of the fluid jet at the outlet of the injection nozzle;

the connecting portion is perpendicular to the injection axis. These arrangements allow improving the performances of the fluid jet at the outlet of the injection nozzle;

the connecting portion forms a shoulder between the first conduit portion and the second conduit portion. A shoulder is less sensitive to manufacturing defects than the bottle-like shape;

the first section has a diameter comprised between 0.8 and 1 millimeter, and in one form the diameter is 1 millimeter. The diameter of the first section thus enables a proper operation of the device while limiting the bulk of the injection nozzle;

the second section has a diameter comprised between 0.3 and 0.45 millimeter, and in one form the diameter is 0.4 millimeter. These arrangements allow for an improved ratio between the first section and the second section;

a ratio of the diameter between the first section and the second section (i.e., second section diameter divided by the first section diameter) is comprised between 0.35 and 0.45 millimeter, and in one form the ratio is equal to 0.4;

the length of the second conduit portion is comprised between 0.5 and 1.5 millimeter. This arrangement allows for a length which is long enough to straighten the current lines of the fluid and short enough to not generate any pressure drop; and/or the nozzle comprises a support configured to receive the at least one conduit, in order to keep the conduit within the injection device.

The present disclosure further relates to a needleless injection device comprising:

a gas generator;

a plunger arranged to be actuated by the gas generator;

a reservoir configured to receive a fluid to be injected, the plunger being configured to eject the fluid out of the reservoir; and at least one injection nozzle in accordance with any one of the aforementioned features, fluidly connected to the reservoir, configured to guide the fluid out of the injection device.

According to an aspect of the present disclosure, the reservoir and the plunger are disposed along the injection axis.

According to an aspect of the present disclosure, the pressure exerted by the gas generator is comprised between 100 and 300 bars.

According to one form, the fluid contained in the reservoir comprises an active ingredient selected from the following active ingredients:

Methotrexate,
Adrenaline,
Sumatriptan,
Hydrocortisone,
Naloxone,
Midazolam,
Apomorphine,
Ethylnatrexone bromide,
Phytomenadione,
Chlorpromazine hydrochloride,
Zuclopenthixol acetate,
Danaparoid sodium,
Enoxaparin sodium,
Estradiol cypionate,
Medroxyprogesterone acetate,
Medroparin calcium,
Methylprednisolone acetate,
Heparin calcium, and
Terbuline.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
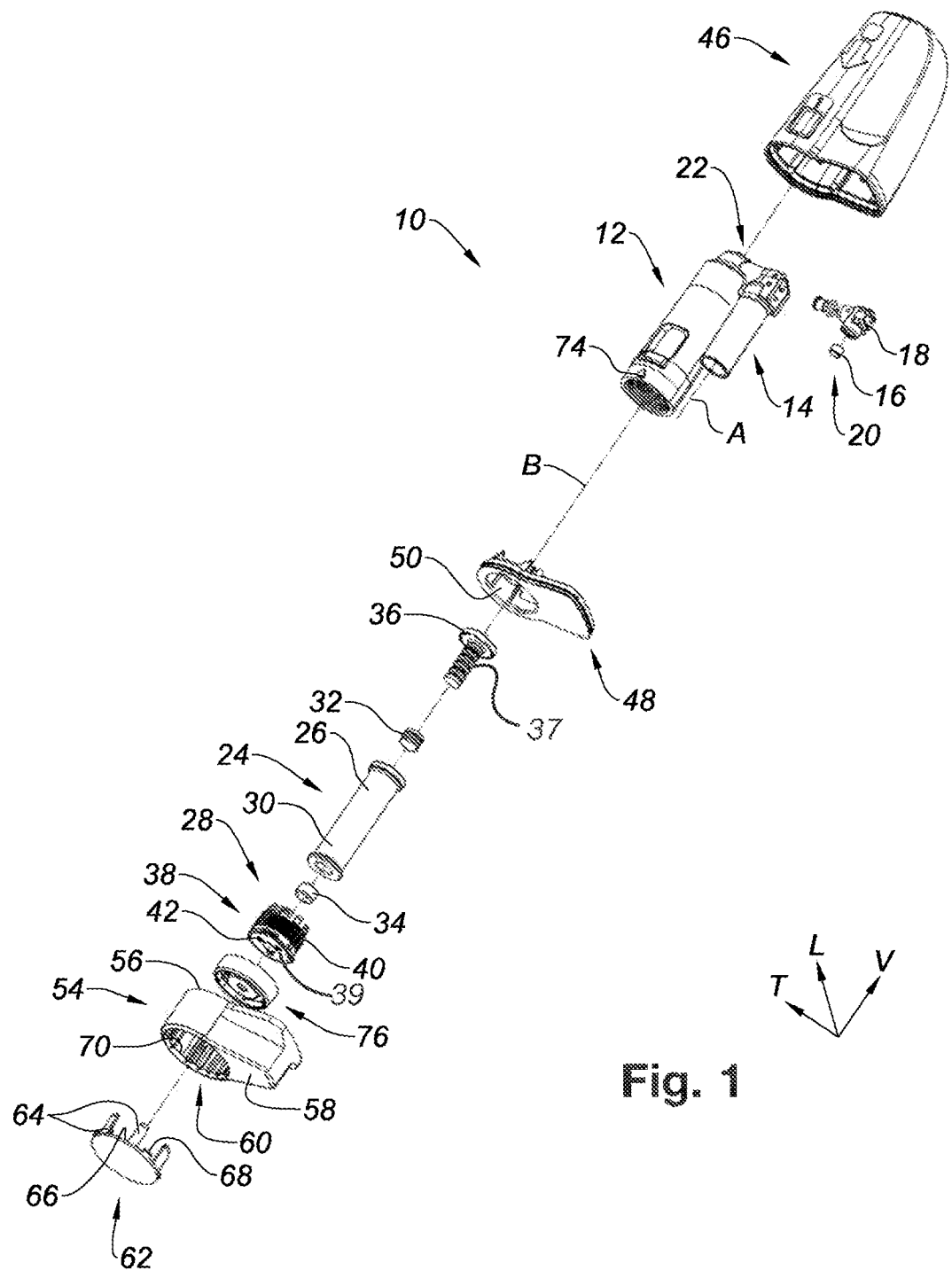
FIG. 1 is an axially exploded perspective view, which illustrates a needleless injection device according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the present disclosure, in order to clarify the description and the claims, the terms longitudinal, vertical and transverse will be used in a non-limiting manner with reference to the trihedron L, V, T indicated in the figures.

It should be noted that in the present patent application, the terms "upstream" and "downstream" should be understood with respect to the circulation of the active ingredient inside the injection device, along an injection direction.

In addition, in the present application, the terms "top," "bottom," "upper," "lower," "horizontal," "vertical," and their derivatives refer to the position or to the orientation of an element or of a component, this position or this orientation being considered with reference to the orientation of the device in the Figures, without reference to Earth's gravity.

There is represented in FIG. 1 a needleless injection device 10, or needleless syringe, which includes a U-shaped body 12 successively comprising a striker device 14, a primer 16, a pyrotechnic charge 18, these three elements constituting a gas generator 20, an expansion chamber 22, a reservoir 24 containing a fluid comprising an active ingredient 26 and an injection system 28.

The gas generator 20 constitutes a linear first subset of the body 12 which extends axially along a vertical first axis A, and the reservoir 24 containing the liquid active ingredient 26 and the injection system 28 form a linear second subset of the body 12 which extends axially along a vertical second injection axis B.

These two subsets are connected to each other by the expansion chamber 22 which has an axis perpendicular to the axes A, B of the subsets.

The reservoir 24 is constituted by a glass tube 30 plugged by an upstream cap-plunger 32 and a downstream cap-plunger 34 between which the liquid active ingredient 26 is contained, the cap-plungers being made of an elastomer-based elastically-deformable material.

The reservoir 24 is inserted into the body 12 and is blocked vertically, on the one hand, at its upstream portion by the body 12, via a cylindrical part 36 made of a flexible material, such as rubber, and provided with a central opening leading onto an elastic pouch 37. The elastic pouch is in fluid communication with the expansion chamber, the gas is then arranged to penetrate into the pouch which then extends by elasticity and thus allows displacing the upstream cap-plunger 32. Thus, the gas does not come into communication with the active ingredient. On the other hand, the reservoir 24 is blocked vertically at its downstream portion by an injection nozzle 38.

Figure 2:
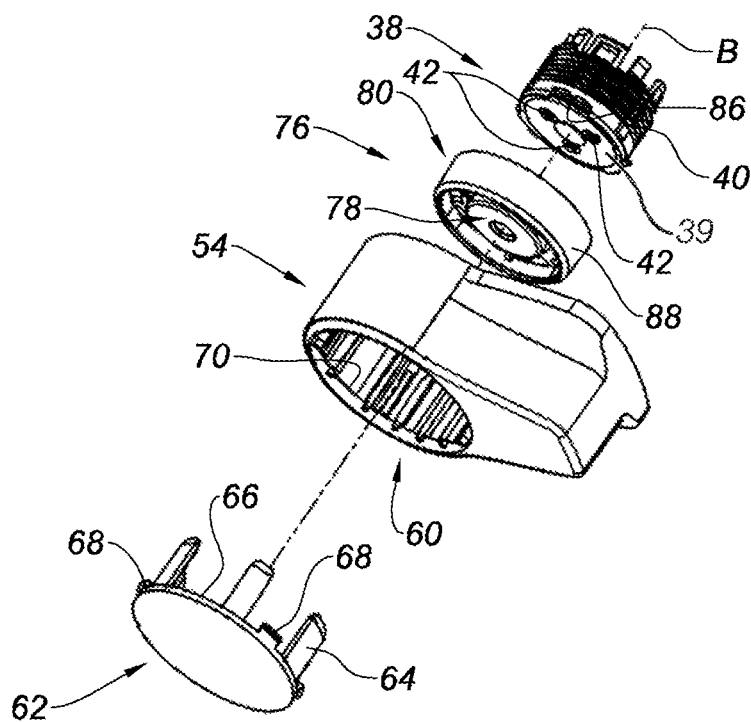
FIG. 2 is a perspective detail view of FIG. 1, which illustrates an injection nozzle comprising outlet conduits according to the present disclosure.

The nozzle 38, shown in more detail in FIG. 2, has a cylindrical shape along the injection axis B which is delimited by a peripheral cylindrical face 40 provided with a tapping, the tapping being intended to cooperate with a complementary thread formed on the inner wall of the downstream end of the body 12.

In addition, the nozzle 38 comprises from one to three outlet conduit(s) 42, parallel to the injection axis B and formed in a support 39.

Figure 3:
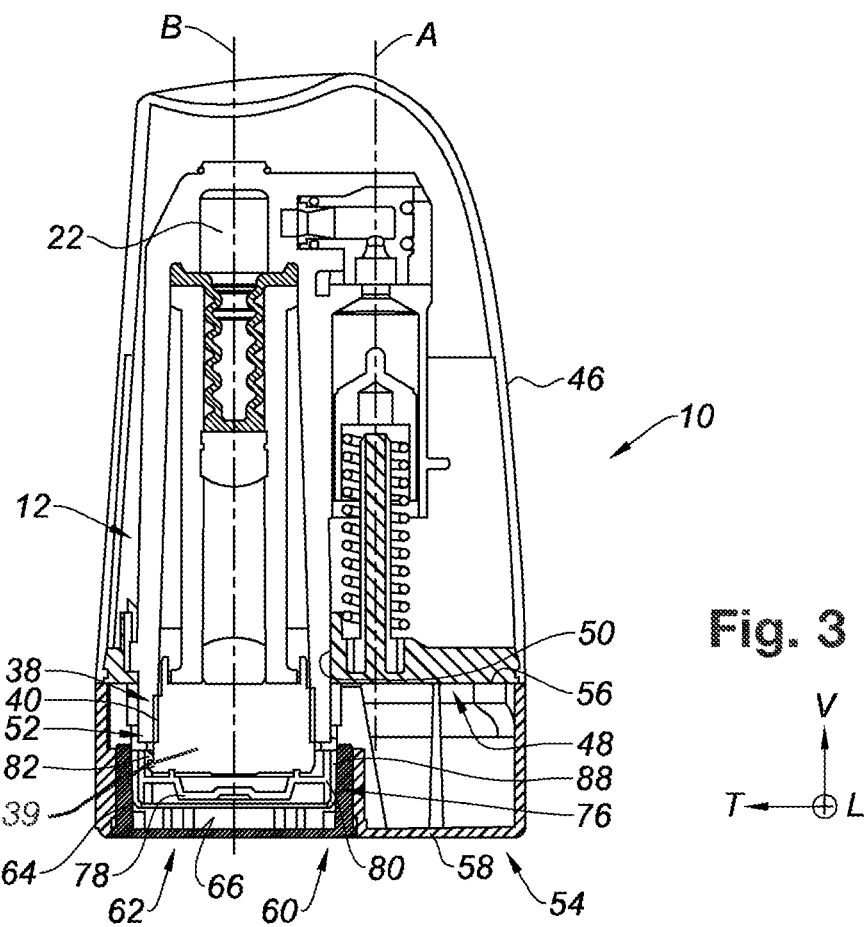
FIG. 3 is an axial sectional view of the injection device according to the present disclosure.

According to FIG. 3, the body 12 is wrapped by a hollow cover 46 which delimits a lower opening closed by a horizontal pad 48 forming a cover bottom.

The pad 48 delimits a circular passage 50 around the injection axis B which is adapted for the passage of the injection nozzle 38 and of the downstream end of the body 12, so that the nozzle 38 includes a lower segment 52 projecting vertically downwards out of the cover 46.

Also, the injection device 10 is equipped with a cap 54 which is delimited vertically by an open upper face 56 bearing on the pad 48 of the cover 46, and a generally planar closed lower face 58.

The cap 54 delimits a generally tubular housing which extends axially along the injection axis B and which opens into the lower face 58 of the cap 54 by forming a circular passage 60 closed by a removable bottom disk 62.

The bottom disk 62 includes six clamping feet 64 which extend axially parallel to the injection axis B, from an upper face 66 of the disk 62.

In addition, in order to enable fastening of the disk 62 on the cap 54, the disk 62 includes four elastically-deformable teeth 68 each adapted to cooperate with an inner annular groove 70 formed by the cap 54.

According to another aspect, the cap 54 is pivotally mounted about the injection axis B between a closure position in which the cap 54 is positioned in the continuation of the cover 46, so that the cap 54 and the cover 46 form a homogeneous shell devoid of any asperity, and an opening position in which the cap 54 is angularly pivoted by about 60 degrees about the injection axis B.

In its closure position, the cap 54 is locked on the rest of the injection device 10. Conversely, in its opening position, the cap 54 is adapted to be removed from the rest of the device 10 to enable access to the nozzle 38 and to carry out an injection.

For this purpose, the injection device 10 includes a first bayonet-type locking device adapted to lock the cap 54 on the body 12 of the device 10, during the driving of the cap 54 between its opening position and its closure position.

Figure 5:
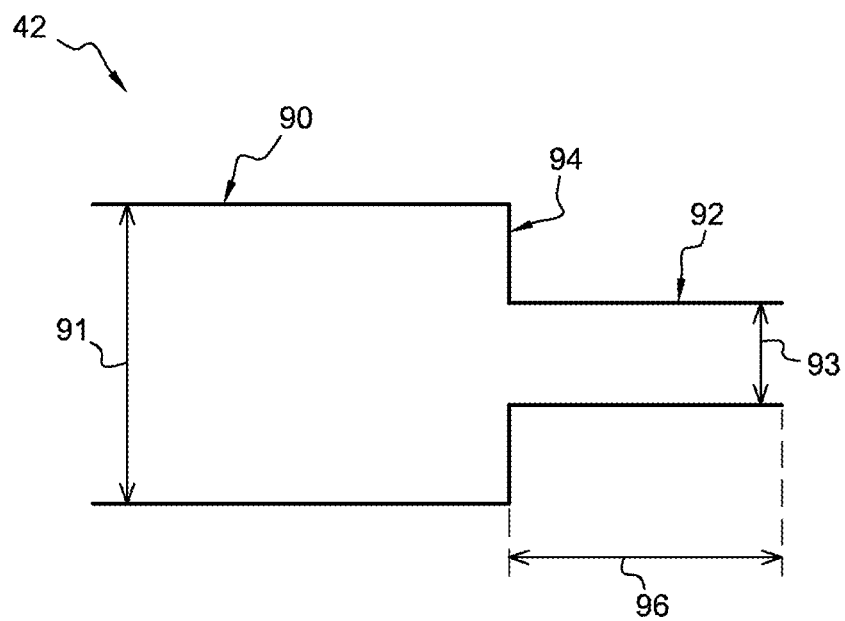
FIG. 5 represents a profile of an outlet conduit according to the present disclosure.

As represented in FIG. 5, the outlet conduits 42 comprising a first conduit portion 90 with a first section 91 and a second conduit portion 92 with a second section 93. The first section 91 being larger than the second section 93. The conduits 42 further comprise a connecting portion 94 between the first conduit portion 90 and the second conduit portion 92. The connecting portion 94 is substantially transversal, that is to say it has an inclination with respect to the injection axis B comprised between 70° and 90°, and in one form is between 80° and 90°. In another form, the connecting portion 94 is perpendicular to the injection axis B.

Figure 4:
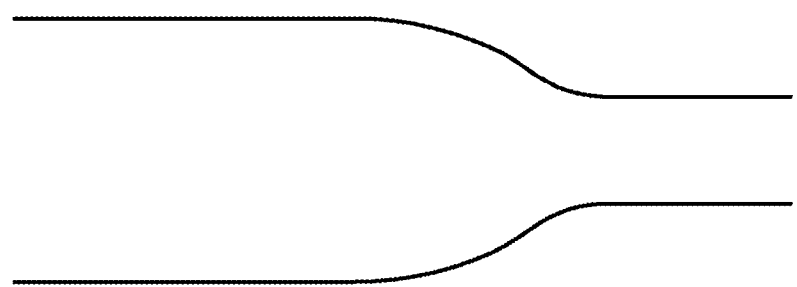
FIG. 4 represents a bottle-like shaped profile of an outlet conduit according to the prior art.

Thus, coherence length of the active ingredient jet is improved. Indeed, the current lines are oriented so as to be substantially parallel to each other over a longer distance, enabling a better penetration and propagation of the product in human tissues. The speed of the active ingredient at the outlet is higher by substantially 10% in comparison with a bottle-like shape, represented in FIG. 4, for the same pressure. Indeed, the bottle-like shape generally allows limiting pressure drops and therefore improving the fluid speed. The consequences of a manufacturing defect are also limited. Furthermore, a connecting portion 94 that is significantly inclined with respect to the injection axis B is more easy to make and less expensive.

Thus, it is possible to obtain a better performance of the jet at the outlet of the injection nozzle with an identical pressure generated by the gas generator or to preserve identical performances while reducing the pressure to be exerted by the gas generator, and thus save energy.

The connecting portion 94 forms a shoulder between the first conduit portion 90 and the second conduit portion 92. A shoulder is less sensitive to manufacturing defects than the bottle-like shape.

The first section 91 has a diameter comprised between 0.8 and 1 millimeter, and in one form the diameter is 1 mm. Thus, the diameter of the first section 91 allows proper operation of the injection device 10 while limiting the bulk in the injection device 10.

The second section 93 has a diameter comprised between 0.3 and 0.45 millimeters, and in one form the diameter is 0.4 millimeter. These arrangements allow for an enhanced ratio between the first section 91 and the second section 93.

The length of the second conduit portion 92 is comprised between 0.5 and 1.5 millimeter. This arrangement allows for a length which is long enough to straighten the current lines of the fluid and short enough to not generate any pressure drop.

For example, the conduits 42 are made of polycarbonate.

As regards the operation of the injection device 10 briefly described later on, this is similar to the operation of the device described in the document FR-A-2815544, which is incorporated by reference herein in its entirety.

The user unlocks the injection device 10 by removing the cap 54 through a rotation in either direction. The user applies the free end of the nozzle 38 against the skin of the patient to be treated and, by pressing with a finger, the user pushes in the cover 46 which slides along the body 12 until triggering of the gas generator 20. The pressure exerted by the gas generator is comprised between 100 and 300 bars.

The generated gases overwhelm the expansion chamber 22 and, when the pressure is sufficient, exert a push on the liquid column constituted by the two cap-plungers 32, 34 and the liquid active ingredient 26, the liquid active ingredient 26 is then expelled by the nozzles 42.

The description of the present disclosure is provided as a non-limiting example.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, manufacturing technology, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device comprising:
    a gas generator;
    a plunger arranged to be actuated by the gas generator;
    a reservoir configured to receive a fluid to be injected, the plunger configured to eject the fluid out of the reservoir; and
    at least one injection nozzle fluidly connected to the reservoir and configured to guide the fluid out of the needleless injection device, the at least one injection nozzle comprising:
        at least one monolithic outlet conduit configured to let the fluid pass when expelled, the at least one outlet conduit extending parallel to an injection axis, the at least one outlet conduit comprising:
            a first conduit portion having a first section;
            a second conduit portion integral with the first conduit portion and having a second section, the first section having a first fluid flow area that is larger than a second fluid flow area of the second section; and
            a connecting portion between the first conduit portion and the second conduit portion, the connecting portion is inclined at an angle comprised between 70° and 90° with respect to the injection axis,
    wherein the gas generator extends along an axis that is offset from the injection axis, and
    wherein the needleless injection device further includes a cap mounted about the injection axis between a closure position in which the cap is locked on the needleless injection device and an open position in which access is allowed to the nozzle to carry out an injection, the cap including a passage at least partially receiving the at least one injection nozzle and closed by a removable disk.

2. The needleless injection device according to claim 1, wherein the reservoir and the plunger are disposed parallel to the injection axis.

3. The needleless injection device according to claim 1, wherein the fluid contained in the reservoir comprises an active ingredient selected from the group consisting of Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medroxyprogesterone acetate, Medroparin calcium, Methylprednisolone acetate, Heparin calcium, and Terbuline.

4. The injection nozzle according to claim 1, wherein the connecting portion is inclined at an angle between 80° and 90° with respect to the injection axis.

5. The injection nozzle according to claim 1, wherein the connecting portion is perpendicular to the injection axis.

6. The injection nozzle according to claim 1, wherein the connecting portion forms a shoulder between the first conduit portion and the second conduit portion.

7. The injection nozzle according to claim 1, wherein the first section of the first conduit portion has a diameter between 0.8 and 1 millimeter.

8. The injection nozzle according to claim 7, wherein the diameter of the first section is 1 millimeter.

9. The injection nozzle according to claim 1, wherein the second section of the second conduit portion has a diameter between 0.3 and 0.45 millimeter.

10. The injection nozzle according to claim 9, wherein the diameter of the second section is 0.4 millimeter.

11. The injection nozzle according to claim 1, wherein a ratio of diameters of the second section to the first section is between 0.35 and 0.45.

12. The injection nozzle according to claim 11, wherein the ratio of diameters is equal to 0.4.

13. The injection nozzle according to claim 1, wherein a length of the second conduit portion is between 0.5 and 1.5 millimeter.

14. The injection nozzle according to claim 1 further comprising a support configured to receive the at least one outlet conduit.

* * * * *